(12) United States Patent
Schubert et al.

(10) Patent No.: US 7,449,594 B2
(45) Date of Patent: *Nov. 11, 2008

(54) PROCESS FOR PREPARING 4-PENTAFLUOROSULFANYLBENZOYL-GUANIDINES

(75) Inventors: Gerrit Schubert, Kelkheim (DE); Heinz-Werner Kleemann, Bischofsheim (DE)

(73) Assignee: Sanofi-aventis Deutschland GmbH, Frankfurt am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/539,237

(22) Filed: Oct. 6, 2006

(65) Prior Publication Data

US 2007/0106094 A1 May 10, 2007

Related U.S. Application Data

(62) Division of application No. 10/988,971, filed on Nov. 15, 2004, now Pat. No. 7,126,026.

(60) Provisional application No. 60/555,466, filed on Mar. 23, 2004.

(30) Foreign Application Priority Data

Nov. 13, 2003 (DE) ................. 103 53 204

(51) Int. Cl.
*C07C 255/50* (2006.01)
*C07C 233/65* (2006.01)
(52) U.S. Cl. ................. 558/415; 564/162; 564/440
(58) Field of Classification Search ........ 564/162, 564/440; 558/415
See application file for complete search history.

(56) References Cited

U.S. PATENT DOCUMENTS

| | | | |
|---|---|---|---|
| 5,591,754 A | 1/1997 | Lang et al. | |
| 5,741,935 A | 4/1998 | Bowden et al. | |
| 5,849,928 A | 12/1998 | Hawkins et al. | |
| 5,851,952 A | 12/1998 | Karp et al. | |
| 5,869,426 A | 2/1999 | Karp et al. | |
| 5,965,491 A | 10/1999 | Wu et al. | |
| 6,080,861 A | 6/2000 | Karp et al. | |
| 6,096,924 A | 8/2000 | Studer et al. | |
| 6,140,528 A | 10/2000 | Hawkins | |
| 6,958,415 B2 | 10/2005 | Lal et al. | |
| 7,015,176 B2 | 3/2006 | Bailey et al. | |
| 7,126,026 B2 * | 10/2006 | Schubert et al. | 564/162 |
| 7,317,124 B2 * | 1/2008 | Kleemann et al. | 562/821 |
| 7,375,138 B2 | 5/2008 | Kleemann | |
| 2005/0202973 A1 | 9/2005 | Schaetzer et al. | |
| 2005/0215785 A1 | 9/2005 | Taylor | |

FOREIGN PATENT DOCUMENTS

| | | |
|---|---|---|
| DE | 10220549 | 12/2002 |
| DE | 10260474 | 7/2003 |
| GB | 2276379 | 9/1994 |
| WO | 88/10251 | 12/1988 |
| WO | 94/21606 | * 9/1994 |
| WO | WO94/21606 | 9/1994 |
| WO | WO02/28182 | 4/2002 |
| WO | WO2005/019377 | 3/2005 |
| WO | WO2005/019378 | 3/2005 |
| WO | WO2005/021488 | 3/2005 |
| WO | WO2005/051390 | 6/2005 |

OTHER PUBLICATIONS

Bowden, R. et. al., A New Method for the Synthesis of Aromatic Sulfurpentafluorides and Studies of the Stability of the Sulfurpentafluoride Group in Common Synthetic Transformations, Tetrahedron 2000, vol. 56 pp. 3399-3408.

Doyle, M. et.al., Alkyl Nitrite-Metal Halide Deamination Reactions. 2. Substitutive Deamination of Arylamine by Alkyl Nitrites and Copper(II) Halides. A Direct and Remarkably Efficient Conversion of Arylamines to Aryl Halides1, J. Org. Chem. 1977, vol. 42, pp. 2426-2430.

Gray, et al., Practical methylation of aryl halides by Suzuki-Miyaura coupling, Tetrahedron Letters; 41; 2000; pp. 6237-6240.

Hassan, J. , Aryl-Aryl Bond Formation One Century after the Discovery of the Ullmann Reaction, Chem. Rev. 2002, 102, pp. 1359-1469.

Kirchhoff, et. al., Boronic Acids: New Coupling Partners in Room-Temperature Suzuki Reactions of Alkyl Bromides. Crystallographic Characterization of an Oxidative-Addition Adduct Generated Under remarkably Mild Conditions, J. Am. Chem. Soc. 2002 vol. 124, pp. 13662-13663.

Larock, R, Comprehensive Organic Transformations: A Guide to Functional Group Preparations Second Edition, Wiley-VCH Publishers, New York, Weinheim 1999, pp. 821-828.

Larock, R., Comprehensive Organic Transformations: A Guide to Functional Group Preparations Second Edition, Wiley-VCH Publishers, New York, Weinheim 1999, pp. 619-628.

Larock, R. et. al., Comprehensive Organic Transformations: A Guide to Functional Group Preparations Second Edition, Wiley-VCH Publishers, New York, Weinheim 1999, pp. 1941-1949.

(Continued)

*Primary Examiner*—Shailendra Kumar
(74) *Attorney, Agent, or Firm*—Raymond S Parker

(57) ABSTRACT

A process for preparing 4-pentafluorosulfanylbenzoylguanidines of formula I wherein R1 to R4 have the meanings indicated in the specification. The compounds of formula I are NEH1 inhibitors and can be employed, for example, for the treatment of cardiovascular disorders.

10 Claims, No Drawings

OTHER PUBLICATIONS

Larock, R. et. al., Comprehensive Organic Transformations: A Guide to Functional Preparations Second Edition, Wiley-VCH Publishers, New York, Weinheim, 1999, pp. 1978-1986.

Larock, R.C. et al, Comprehensive Organic Transformations: A Guide to Functional Group Preparations Second Edition, Wiley-VCH Publishers, New York, Weinheim, 1999, pp. 678-679.

Miyaura, Norio et al., Palladium-Catalyzedd Cross-Coupling Reactions of Organoboron Compounds, Chem Review, 1995, 95, (7), pp. 2457-2483.

Netherton, M. et., al., Room-Temperature Alkyl-Alkyl Suzuki Cross-Coupling of Alkyl Bromides that Possess B Hydrogens, J. Am. Chem. Soc. 2001, 123, pp. 10099-10100.

Oae, S, et. al., Direct Conversion of Arylamines to the Halides by Deamination with Thionitrite or Related Compounds and Anhydrous Copper(II) Halides, Bull. Chem. Soc. Jpn. 1980, vol. 53, 1065-1069.

Sheppard William A., Arylsulfur Pentafluorides, Journal of the American Chemical Society; vol. 84; No. 16; (Aug. 20, 1962); pp. 3064-3072.

Smith, M.B., March's Advanced Organic Chemistry: Reactions, Mechanisms, and Structure, Wiley, New York, 2001, 704-707.

Smith, M.B. et. al., March's Advanced Organic Chemistry: Reactions, Mechanisms, and Structure, Wiley, New York, 2001, pp. 506-516.

Smith, M.B. et. al., March's Advanced Organic Chemistry: Reactions, Mechanisms, and Structure, Wiley, New York, 2001, pp. 935-936.

Smith, M.B. et. al., March's Advanced Organice Chemistry: Reactions, Mechanisms, and Structure, Wiley, New York, 2001, pp. 1179-1180.

Stanforth, Stephen P., Catalytic Cross-coupling Reactions in Biaryl Synthesis, Tetrahedron, 54, (3/3), 1998, pp. 263-303.

\* cited by examiner

PROCESS FOR PREPARING 4-PENTAFLUOROSULFANYLBENZOYL-GUANIDINES

CROSS-REFERENCE TO RELATED APPLICATIONS

This application is a divisional of application Ser. No. 10/988,971 filed on Nov. 15, 2004, now U.S. Pat. No. 7,126,026 which claims the benefit of priority under 35 U.S.C. § 119 from German patent application No. 10353204.8, filed on Nov. 13, 2003, the contents of which are hereby incorporated by reference, which claims the benefit of priority under 35 U.S.C. § 119(e) from U.S. provisional application Ser. No. 60/555,466, filed on Mar. 23, 2004, the contents of which are hereby incorporated by reference.

FIELD OF THE INVENTION

The present invention relates to a process for preparing 4-pentafluorosulfanylbenzoylguanidines having the structure defined by formula I. Such compounds are NHE1 inhibitors and can be employed, for example, for the treatment of cardiovascular disorders.

BACKGROUND OF THE INVENTION

DE application 10222192 describes pentafluorosulfanylbenzoylguanidines as NHE1 inhibitors. The processes described therein for preparing these compounds, however, result in low yield and require reagents and reaction conditions that necessitate great technical complexity or are unsuitable for preparation on a relatively large scale. It has now been found that said disadvantages can be avoided by a novel efficient synthesis which starts from commercially available 4-nitrophenylsulfur pentafluoride.

SUMMARY OF THE INVENTION

In one embodiment, the present invention relates to a process for preparing compound of the formula I

I wherein:

R1 is hydrogen, alkyl having 1, 2, 3 or 4 carbon atoms, alkoxy having 1, 2, 3 or 4 carbon atoms, NR10R11, —O—$(CH_2)_n$—$(CF_2)_o$—$CF_3$ or —$(SO_m)_q$—$(CH_2)_r$—$(CF_2)_s^p$—$CF_3$;

R10 R11 are, independently of one another, hydrogen, alkyl having 1, 2, 3 or 4 carbon atoms or —$CH_2$—$CF_3$;

m is zero, 1 or 2 n, o, p q, r and s are, independently of one another, zero or 1;

R2 is hydrogen, —$(SO_h)_z$—$(CH_2)_k$—$(CF_2)_l$—$CF_3$, alkyl having 1, 2, 3, 4, 5 or 6 carbon atoms, cycloalkyl having 3, 4, 5, 6, 7 or 8 carbon atoms, in which 1, 2, 3 or 4 hydrogen atoms may be replaced by fluorine atoms;

h is zero, 1 or 2;

z is zero or 1;

k is zero, 1, 2, 3 or 4;

l is zero or 1;

or R2 is —$(CH_2)_t$-phenyl or —O-phenyl, which are unsubstituted or substituted by 1, 2 or 3 radicals selected from the group consisting of —$O_u$—$(CH_2)_v$—$CF_3$, alkoxy having 1, 2, 3 or 4 carbon atoms, alkyl having 1, 2, 3 or 4 carbon atoms and —$SO_2CH_3$;

t is zero, 1, 2, 3 or 4;

u is zero or 1;

v is zero, 1, 2 or 3;

or R2 is —$(CH_2)_2$-heteroaryl which is unsubstituted by 1, 2 or 3 radicals selected from the group consisting of —$O_x$—$(CH_2)_y$—$CF_3$, alkoxy having 1, 2, 3 or 4 carbon atoms and alkyl having 1, 2, 3 or 4 carbon atoms, —$SO_2CH_3$;

w is zero, 1, 2, 3 or 4;

x is zero or 1;

y is zero, 1, 2 or 3; and

R3 and R4, independently of one another, are hydrogen or F;

and the salts thereof;

which comprises, as depicted in scheme I,

Scheme 1

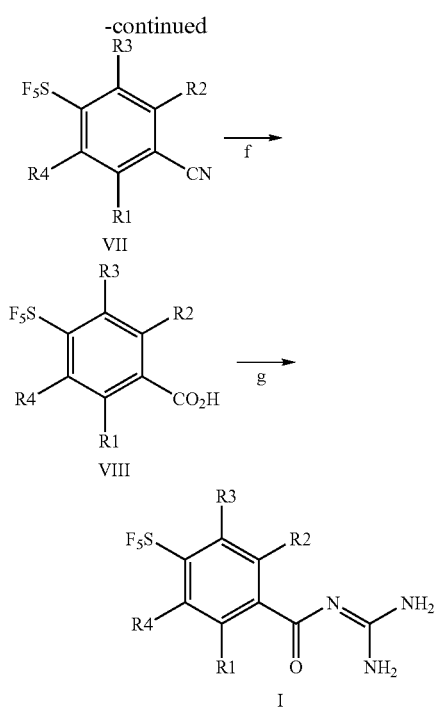

a) reducing a 4-nitrophenylsulfur pentafluoride derivative of the formula II to the amine of formula III, and b) halogenating the compound of the formula III in the ortho position to the amino group with a halogenating agent to give the compound of the formula IV, and c) replacing the halogen substituent in the compound of the formula IV with a suitable nucleophile or an organometalic compound, for example an alkylboron compound, where appropriate with catalysis, by a substituent R2, and d) replacing the amino function in the compound of the formula V by a halogen substituent and e) replacing the halogen substituent in the compound of the formula VI by a nitrile function, and f) hydrolyzing the nitrile function of the compound of the formula VII to the carboxylic acid, and g) converting the carboxylic acid of the formula VIII into the acylguanidine of the formula I, wherein in the compounds of the formulae II, III, IV, V, VI, VII and VIII, R1 to R4 are as defined in formula I and X and Y are, independently of one another, F, Cl, Br or I.

In this process, the steps a), b), c), d), e), f), g), and h) may be performed independently of one another, continuously or discontinuously. For example, steps a)-h) may be performed sequentially without interruption. Alternatively, certain steps may be performed in one period of time, followed by other steps performed at a later period of time.

In another embodiment of the present invention, preferred compounds include compounds of formula I wherein R1 is hydrogen, alkyl having 1, 2, 3 or 4 carbon atoms, methoxy, ethoxy, NR10R11, —O—CH$_2$—CF$_3$ or —SO$_m$—(CH$_2$)$_r$—CF$_3$, wherein R10 and R11 are, independently of one another, hydrogen, alkyl having 1, 2, 3 or 4 carbon atoms or —CH$_2$—CF$_3$, and where m is zero, 1 or 2 and r is zero or 1.

In yet another embodiment of the present invention, preferred compounds include compounds of formula I wherein R1 is hydrogen or methyl.

In yet another embodiment of the present invention, preferred compounds include compounds of formula I wherein R2 is hydrogen, alkyl having 1, 2, 3 or 4 carbon atoms or —SO$_h$—(CH$_2$)$_k$—CF$_3$ here h is zero, 1 or 2 and k is zero or 1, phenyl or —O-phenyl, which are unsubstituted or substituted as indicated, with particular preference for compounds wherein R2 is hydrogen or methyl.

In a further embodiment of the invention, preferred compounds of formula I include compounds wherein R3 and R4 are hydrogen.

In preferred embodiments, the procedure for preparing the compounds of formula I (Scheme 1) is to first convert the compounds of formula II into compounds of formula III by methods known in principle for the reduction of aromatic nitro compounds to aromatic amines (step a). Such methods are described in, for example, R. C. Larock, Comprehensive Organic Transformations: A Guide to Functional Group Preparations, VCH Publishers, New York, Weinheim, 1999, 821-828 and the literature cited therein.

Subsequently, in step b, the compounds of formula III are dissolved in an organic solvent A and reacted with a halogenating agent such as, for example, a brominating agent. In one embodiment of the invention, the reaction temperature in this case is preferably from –30° C. to +150° C., and more preferably from 0° C. to 40° C. The reaction time is generally from 10 min to 20 h, depending on the composition of the mixture and the chosen temperature range. The resulting reaction mixture can be worked up by subsequent filtration through a layer of silica gel, washing with organic solvent A and, after removal of the solvent in vacuo, purifying the product by conventional purification methods such as recrystallization, distillation or chromatography.

Typically, from 0.1 to 10 mol of the compound of formula II for example are dissolved in 1000 ml of organic solvent A. For example, from 0.8 to 1.2 equivalents of the halogenating agent are used for 1 mol of the compound of formula II to be halogenated.

The term "halogenating agent" means for example elemental halogens, halogen-amine complexes, cyclic and acyclic N-halogenated carboxamides and -imides, and ureas, as described, for example, in R. C. Larock, Comprehensive Organic Transformations: A Guide to Functional Group Preparations, VCH Publishers, New York, Weinheim, 1999, 619-628, and the literature cited therein or M. B. Smith and J. March, March's Advanced Organic Chemistry: Reactions, Mechanisms, and Structure, Wiley, New York, 2001, 704-707, and the literature cited therein, such as, for example, N-bromosuccinimide, N-chlorosuccinimide, HBr in H$_2$SO$_4$ or 1,3-dibromo-5,5-dimethylimidazolidine-2,4-dione, the latter being able to transfer 2 bromine atoms per molecule. The term "brominating agent" means, for example, elemental bromine, bromine-amine complexes, cyclic and acyclic N-brominated carboxamides and -imides, and ureas, as described, for example, in R. C. Larock, Comprehensive Organic Transformations: A Guide to Functional Group Preparations, VCH Publishers, New York, Weinheim, 1999, 622-624, and the literature cited therein or M. B. Smith and J. March, March's Advanced Organic Chemistry: Reactions, Mechanisms, and Structure, Wiley, New York, 2001, 704-707, and the literature cited therein, for example N-bromosuccinimide, HBr in H$_2$SO$_4$ or 1,3-dibromo-5,5-dimethylimidazolidine-2,4-dione, the latter being able to transfer 2 bromine atoms per molecule.

The term "organic solvent A" preferably means aprotic solvents such as, for example, dichloromethane, chloroform, tetrachloromethane, pentane, hexane, heptane, octane, benzene, toluene, xylene, chlorobenzene, 1,2-dichloroethane, trichloroethylene or acetonitrile.

Any HX produced in the reaction can be trapped by organic or inorganic bases.

In step c, the compounds of formula IV are subsequently dissolved in an organic solvent B and reacted with a nucleophile R2⁻ or an element compound comprising the substituent R2 to give compounds of the formula V. Optionally, it is possible to add a base A and to add a catalyzing metal salt A.

In one embodiment of the invention, the reaction temperature is preferably between −20° C. and +150° C., and more preferably between 30° C. and 100° C. The reaction time is generally from 0.5 h to 20 h, depending on the composition of the mixture and the chosen temperature range. The resulting reaction mixture can be worked up by subsequent filtration through a layer of silica gel, washing with an organic solvent B and, after removal of the solvent in vacuo, purifying the product by conventional purification processes such as recrystallization, chromatography, for example on silica gel, distillation or stream distillation.

Typically, from 0.1 to 10 mol of the compound of formula IV for are dissolved in 1000 ml of organic solvent B. For example, from 0.8 to 3 equivalents of the nucleophile R2⁻ or of the element compound comprising the substituent R2 are used for 1 mol of the starting compound of formula IV.

As used herein, the term "nucleophile R2" means compounds which result on deprotonation of a compound R2—H with strong bases such as, for example, alkyl- or aryllithium compounds, organomagnesium compounds, alcoholates or lithium diisopropylamide.

As used herein, the term "organometallic" means of, relating to, or being an organic compound that usually contains a metal or metalloid bonded directly to a carbon atom. Thus, the phrase "organometalic compounds comprising the substituent R2" means, for example, organometallic compounds wherein the metal is bonded to a carbon atom of an R2 group wherein the R2 group is as previously defined. Examples include, for example, organolithium compounds R2—Li, organomagnesium compounds R2—Mg-Hal with Hal=Cl, Br, I, organoboron compounds such as R2—B(OH)$_2$, R2-boronic esters such as, for example,

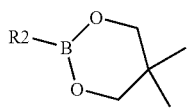

R2-boronic anhydrides such as, for example,

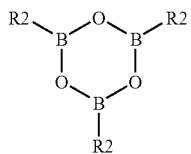

or organozinc compounds R2—Zn-Z, with Z=Cl, Br, I.

The term "base A" means bases like those used as auxiliary bases in cross-coupling reactions and mentioned for example in A. Suzuki et al., Chem. Rev. 1995, 95, 2457-2483 or M. Lamaire et al., Chem. Rev. 2002, 102, 1359-1469 or S. P. Stanforth, Tetrahedron 1998, 54, 263-303 and the literature cited therein in each case, for example Na$_2$CO$_3$, Cs$_2$CO$_3$, KOH, NaOH, K$_3$PO$_4$, N(ethyl)$_3$.

The term "organic solvent B" means protic or aprotic solvents such as diethyl ether, dimethoxyethane, THF, alcohols, water or mixtures thereof. In one embodiment, mixtures with water are preferred.

The term "catalyzing metal salt A" means inter alia Pd and Ni catalysts like those used for Suzuki and Negishi reactions and described for example in A. Suzuki et al., Chem. Rev. 1995, 95, 2457-2483 or M. Lamaire et al., Chem. Rev. 2002, 102, 1359-1469 or S. P. Stanforth, Tetrahedron 1998, 54, 263 or G. C. Fu et al., J. Am. Chem. Soc. 2001, 123, 10099 or G. C. Fu et al., J. Am. Chem. Soc. 2002, 124, 13662 and the literature cited therein in each case, including the added ligands such as Pd(OAc)$_2$, PdCl$_2$(dppf) or Pd$_2$(dba)$_3$.

In step d, the compounds of formula V are subsequently converted into the compounds of formula VI by a diazotization-halogenation process with a diazotizing-halogenating agent, for example with a diazotizing-brominating agent, as described for other aromatic amines to replace the amine function by a halogen function for example in M. B. Smith and J. March, March's Advanced Organic Chemistry: Reactions, Mechanisms, and Structure, Wiley, New York, 2001, 935-936 or R. C. Larock, Comprehensive Organic Transformations: A Guide to Functional Group Preparations, VCH Publishers, New York, Weinheim, 1999, 678-679 and the literature cited therein, for example by the Sandmeyer or Gattermann reaction. The process of M. Doyle et al., J. Org. Chem. 1977, 42, 2426 or of S. Oae et al., Bull. Chem. Soc. Jpn. 1980, 53, 1065 is preferred.

In step e, the compounds of formula VI are reacted in a solvent C with a cyanidating agent, for example with addition of a catalyzing metal salt B. In one embodiment of the invention, the reaction temperature is preferably from 20° C. to 200° C., and more preferably from 80° C. to 150° C. The reaction time is generally from 1 h to 20 h, depending on the composition of the mixture and the chosen temperature range. The resulting reaction mixtures can be filtered with suction through a layer of silica gel or kieselguhr and the filtrate can be worked up by aqueous extraction. After evaporation of the solvent in vacuo, the compound of formula VII is purified by conventional purification processes such as recrystallization, chromatography on silica gel, distillation or steam distillation.

Typically, from 0:1 to 10 mol of the compound of formula VI are dissolved in 1000 ml of organic solvent C. For example, from 1 to 10 equivalents of the cyanidating agents are used for 1 mol of the compound having the formula VI to be reacted.

The term "cyanidating agent" means, for example, alkali metal cyanides or Zn(CN)$_2$ either alone or mixed with metallic zinc, preferably in the form of zinc dust.

The term "organic solvent C" preferably means aprotic polar solvents such as, for example, DMF, dimethylacetamide, NMP, DMSO.

The term "catalyzing metal salt B" means inter alia Pd and Ni catalysts like those employed in Suzuki reactions and described for example in A. Suzuki et al., Chem. Rev. 1995, 95, 2457-2483 or M. Lamaire et al., Chem. Rev. 2002, 102, 1359-1469 or S. P. Stanforth, Tetrahedron 1998, 54, 263 and the literature cited therein, for example PdCl$_2$(dppf), Pd(OAc)$_2$, Pd$_2$(dba)$_3$.

The resulting compounds of formula VII are subsequently hydrolyzed in step f to the carboxylic acids of formula VIII, for example in the presence of a base. This can take place by processes known to the skilled worker for hydrolyzing aromatic nitriles, as described, for example, in R. C. Larock, comprehensive Organic Transformations: A Guide to Functional Group Preparations, VCH Publishers, New York, Weinheim, 1999, 1986-1987 or M. B. Smith and J. March, March's Advanced Organic Chemistry: Reactions, Mechanisms, and Structure, Wiley, New York, 2001, 1179-1180 and the literature cited therein.

In step g, the carboxylic acids of formula VIII are then subsequently converted into the acylguanidines having formula IX. For this purpose, the carboxylic acids are converted into activated acid derivatives such as carbonyl halides, preferably carbonyl chlorides, esters, preferably methyl esters, phenyl esters, phenylthio esters, methylthio esters, 2-pyridylthio esters, or a nitrogen heterocycle, preferably 1-imidazolyl. The esters and nitrogen heterocycles are advantageously obtained in a manner known to the skilled worker from the underlying carbonyl chlorides, which in turn themselves can be prepared in a known manner from the underlying carboxylic acids, for example with thionyl chloride.

Besides the carbonyl chlorides, it is also possible to prepare other activated acid derivatives in a known manner directly from the underlying benzoic acids, such as the methyl esters by treatment with gaseous HCl in methanol, the imidazolides by treatment with carbonyldiimidazole the mixed anhydrides with Cl—$COOC_2H_5$ or tosyl chloride in the presence of triethylamine in an inert solvent, as well as activations of benzoic acids with dicyclohexylcarbodimide (DCC) or with O-[(cyano(ethoxycarbonyl)methylene)amino]-1,1,3,3-tetramethyluronium tetrafluoroborate ("TOTU") are possible. A number of suitable methods for preparing activated carboxylic acid derivatives are indicated with indication of source literature M. B. Smith and J. March, March's Advanced Organic Chemistry: Reactions, Mechanisms, and Structure, Wiley, New York, 2001, 506-516 or R. C. Larock, Comprehensive Organic Transformations: a Guide to Functional Group Preparations, VCH Publishers, New York, Weinheim, 1999, 1941-1949.

Reaction of an activated carboxylic acid derivative with guanidine preferably takes place in a manner known per se in a protic or aprotic polar but inert organic solvent either with free guanidine base or with guanidinium chloride in the presence of a base. In this connection, methanol, isopropanol or THF at temperatures from 20° C. to the boiling point of these solvents have proved suitable for the reaction of the methyl benzoates with guanidine. Most reactions of carboxylic acid derivatives with salt-free guanidine are advantageously carried out in aprotic inert solvents such as THF, dimethoxyethane, dioxane. However, water can also be used as solvent in the reaction with guanidine on use of a base such as, for example, NaOH.

If a carbonyl chloride is employed as carboxylic acid derivative, it is advantageous to add an acid scavenger, for example in the form of excess guanidine, to bind the hydrohalic acid.

For preparing compounds of formula I in which R2 is hydrogen, the synthesis occurs as described in Scheme 1, however, without steps b and c.

In order to prepare compounds of formula I with R2=—$(SO_h)_z$—$(CH_2)_k$—$(CF_2)_l$—$CF_3$, where h is 1 or 2, as described above, compounds in which R2 is —$(SO_h)_z$—$(CH_2)_k$—$(CF_2)_l$—$CF_3$, where h is zero, are synthesized and subsequently converted by generally known oxidation reactions into the desired compounds of formula I.

The reaction mixture can be worked up after each of process steps a), b), c), d), e), f) and g) or after two or more process steps. Synthesis of the compounds of formula I by the process of the invention can, however, also take place in two or more consecutive process steps without isolation of the compounds III, IV, V, VI, VII or VIII obtained in the individual process steps, in which case workup after each process step is unnecessary. The workup and, if desired, the purification of the products takes place by the usual methods such as extraction, pH separation, chromatography or crystallization and the usual dryings.

The starting compounds of formula II are obtainable by purchase or can be prepared by or in analogy to processes described in the literature and known to the skilled worker, for example as described in Bowden, R. D., Comina, P. J., Greenhall, M. P., Kariuki, B. M., Loveday, A., Philip, D. Tetrahedron 2000, 56, 5660. Functional groups in the starting compounds may also be present in protected form or in the form of precursors, and then be converted into the desired groups in the compounds of formula I prepared by the process of the invention. Appropriate protective group techniques are known to the skilled worker. For example, the $NH_2$ group in compounds of formula II in which R1 is $NH_2$ can be present in a form protected by an acetyl, trifluoroacetyl or trityl group and be deprotected again.

A further aspect of the invention relates to novel compounds of formulae V, VI, VII, VIII and IX.

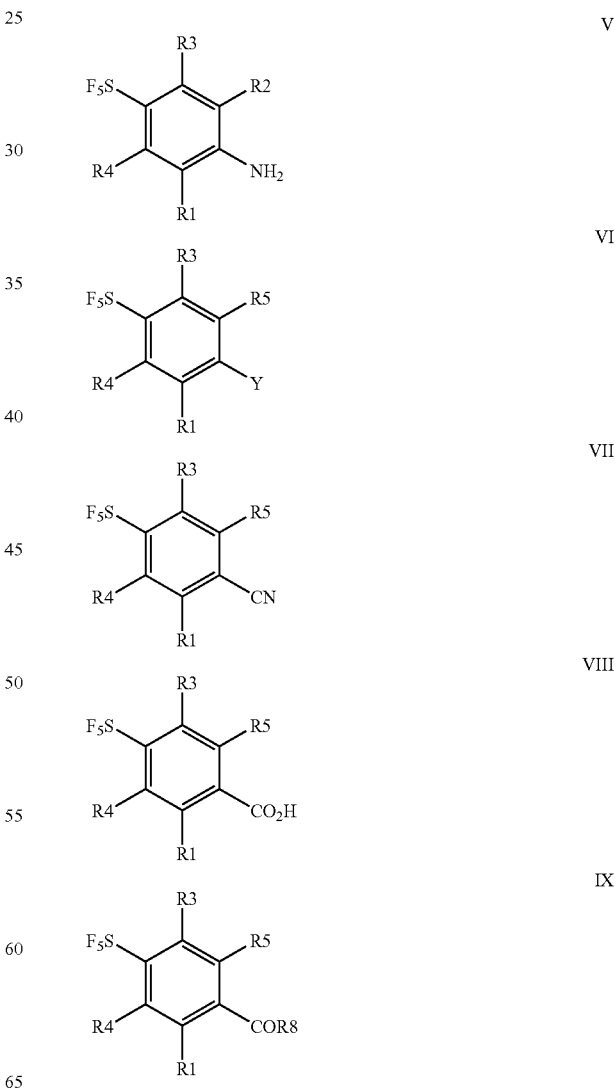

Another embodiment of the present invention, thus relates to 4-pentafluorosulfanyl-substituted compounds of the formula X

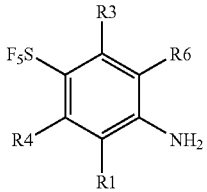

wherein:

R1 is hydrogen, alkyl having 1, 2, 3 or 4 carbon atoms, alkoxy having 1, 2, 3 or 4 carbon atoms, NR10R11, —O—(CH$_2$)$_n$—(CF$_2$)$_o$—CF$_3$ or —(SO$_m$)$_q$—(CH$_2$)$_s$—CF$_3$;

R10 and R11 are, independently of one another, hydrogen, alkyl having 1, 2, 3 or 4 carbon atoms or —CH$_2$—CF$_3$;

m is zero, 1 or 2;

n, o, p, q, r and s are, independently of one another, zero or 1;

R6 is —(SO$_h$)$_z$—(CH$_2$)$_k$—(CF$_2$)$_l$—CF$_3$, alkyl having 1, 2, 3, 4, 5 or 6 carbon atoms, cycloalkyl having 3, 4, 5, 6, 7 or 8 carbon atoms, in which 1, 2, 3 or 4 hydrogen atoms may be replaced by fluorine atoms;

h is zero, 1 or 2;

z is zero or 1;

k is zero, 1, 2, 3 or 4;

l is zero or 1;

or R6 is —(CH$_2$)$_t$-phenyl or —O-phenyl, which are unsubstituted or substituted by 1, 2 or 3 radicals selected from the group consisting of —O$_u$—(CH$_2$)$_v$—CF$_3$, alkoxy having 1, 2, 3 or 4 carbon atoms, alkyl having 1, 2, 3 or 4 carbon atoms, —SO$_2$CH$_3$;

t is zero, 1, 2, 3 or 4;

u is zero or 1;

v is zero, 1, 2 or 3;

or R6 is —(CH$_2$)$_w$-heteroaryl which is unsubstituted or substituted by 1, 2 or 3 radicals selected from the group consisting of —O$_x$—(CH$_2$)$_y$—CF$_3$, alkoxy having 1, 2, 3 or 4 carbon atoms and alkyl having 1, 2, 3 or 4 carbon atoms, —SO$_2$CH$_3$;

w is zero, 1, 2, 3 or 4;

x is zero or 1;

y is zero, 1, 2 or 3; and

R3 and R4, independently of one another, are hydrogen or F;

and the salts thereof.

In one embodiment of the present invention, preferred compounds of formula X are compounds wherein R1 is hydrogen, alkyl having 1, 2, 3 or 4 carbon atoms, methoxy, ethoxy, NR10R11, —O—CH$_2$—CF$_3$ or —SO$_m$—(CH$_2$)$_r$—CF$_3$, where R10 and R11 are independently of one another hydrogen, alkyl having 1, 2, 3 or 4 carbon atoms or —CH$_2$—CF$_3$, and where m is zero, 1 or 2 and r is zero or 1.

Particularly preferred compounds of formula X are those wherein R1 is hydrogen or methyl.

In a further embodiment, preferred compounds of formula X are compounds wherein R6 is hydrogen, F, Cl, Br, I, alkyl having 1, 2, 3 or 4 carbon atoms or —SO$_h$—(CH$_2$)$_k$—CF$_3$, where h is zero, 1 or 2 and k is zero or 1, phenyl or —O-phenyl, which are unsubstituted or substituted as indicated, with particular preference for compounds wherein R6 is hydrogen or methyl.

In a further embodiment, preferred compounds of formula X are compounds wherein R6 is F, Cl, Br or I. It is particularly preferred when R6 is Br.

In yet a further embodiment, preferred compounds of formula X are compounds wherein R3 and R4 are hydrogen.

Another embodiment of the present invention relates to 4-pentafluorosulfanyl-substituted compounds of the formula XI

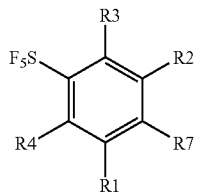

wherein:

R1 is hydrogen, alkyl having 1, 2, 3 or 4 carbon atoms, alkoxy having 1, 2, 3 or 4 carbon atoms, NR10R11, —O—(CH$_2$)$_n$—(CF$_2$)$_o$—CF$_3$ or —(SO$_m$)$_q$—(CH$_2$)$_r$—(CF$_2$)$_s^p$—CF$_3$;

R10 and R11 are, independently of one another, hydrogen, alkyl having 1, 2, 3 or 4 carbon atoms or —CH$_2$—CF$_3$;

m is zero, 1 or 2;

n, o, p, q, r and s are, independently of one another, zero or 1;

R2 is hydrogen, F, Cl, Br, I, —(SO$_h$)$_z$—(CH$_2$)$_k$—(CF$_2$)$_l$—CF$_3$ or alkyl having 1, 2, 3, 4, 5, or 6 carbon atoms;

h is zero, 1 or 2;

z is zero or 1;

k is zero, 1, 2, 3 or 4;

l is zero or 1;

R3 and R4 are, independently of one another hydrogen or F; and

R7 is CN, and the salts thereof.

In another embodiment of the present invention, preferred compounds of formula XI are compounds wherein R1 is hydrogen, alkyl having 1, 2, 3 or 4 carbon atoms, methoxy, ethoxy, NR10R11, —O—CH$_2$—CF$_3$ or —SO$_m$—(CH$_2$)$_r$—CF$_3$, wherein R10 and R11 are independently of one another hydrogen, alkyl having 1, 2, 3 or 4 carbon atoms or —CH$_2$—CF$_3$, and where m is zero, 1 or 2 and r is zero or 1, with particular preference for compounds in which R1 is hydrogen or methyl. In a further embodiment, preference is given to compounds of formula XI in which R2 is hydrogen, F, Cl, Br, I, alkyl having 1, 2, 3 or 4 carbon atoms or —SO$_h$—(CH$_2$)$_k$—CF$_3$, which h is zero, 1 or 2 and k is zero or 1, with particular preference for compounds in which R2 is hydrogen or methyl, preferably hydrogen. In a further embodiment, preference is given to compounds of formula XI in which R2 is F, Cl, Br or I, preferably Br.

In a further embodiment, preference is given to compounds of formula XI in which R3 and R4 are hydrogen.

If the substituents R1, R2, R3, R4 and R6 contain one or more centers of asymmetry, these may have independently of one another either the S or R configuration. The compounds can exist as optical isomers, as diastereomers, as racemates or mixtures thereof in all ratios. Compounds of the formulae X and XI are useful as intermediates, for example, in the synthesis of compounds of formula I.

The present invention encompasses all tautomeric forms of the compounds of the formula I.

Alkyl radicals may be straight-chain or branched. This also applies if they carry substituents or occur as substituents of other radicals, for example in fluoroalkyl radicals or alkoxy radicals. Examples of alkyl radicals are methyl, ethyl, n-propyl, isopropyl (=1-methylethyl), n-butyl, isobutyl (=2-methylpropyl), sec-butyl (=1-methylpropyl), tert-butyl (=1,1-dimethylethyl), n-pentyl, isopentyl, tert-pentyl, neopentyl and hexyl. In one embodiment, preferred alkyl radicals include methyl, ethyl, n-propyl and isopropyl. One or more, for example 1, 2, 3, 4 or 5, hydrogen atoms in alkyl radicals may be replaced by fluorine atoms. Examples of such fluoroalkyl radicals include trifluoromethyl, 2,2,2-trifluoroethyl and pentafluoroethyl. Substituted alkyl radicals may be substituted in any positions.

Examples of cycloalkyl radicals are cyclopropyl, cyclobutyl, cyclopentyl, cyclohexyl, cycloheptyl or cyclooctyl. One or more, for example 1, 2, 3 or 4, hydrogen atoms in cycloalkyl radicals may be replaced by fluorine atoms. Substituted cycloalkyl radicals may be substituted in any positions.

Phenyl radicals may be unsubstituted or be substituted one or more times, for example once, twice or three times, by identical or different radicals. In one embodiment, if a phenyl radical is substituted, it preferably has one or two identical or different substituents. This likewise applies to substituted phenyl radicals in groups such as, for example, phenylalkyl or phenyloxy. The substituent in monosubstituted phenyl radicals may be in position 2, position 3 or position 4. Disubstituted phenyl may be substituted in the 2,3 position, 2,4 position, 2,5 position, 2,6 position, 3,4 position or 3,5 position. The substituents in trisubstituted phenyl radicals may be in the 2,3,4 position, 2,3,5 position, 2,4,5 position, 2,4,6 position, 2,3,6 position or 3,4,5 position. Heteroaryl radicals are aromatic ring compounds in which one or more ring atoms are oxygen atoms, sulfur atoms or nitrogen atoms, e.g. 1, 2 or 3 nitrogen atoms, 1 or 2 oxygen atoms, 1 or 2 sulfur atoms or a combination of various heteroatoms. The heteroaryl radicals may be attached by all positions, for example by the 1 position, 2 position, 3 position, 4 position, 5 position, 6 position, 7 position or 8 position. Heteroaryl radicals may be unsubstituted or be substituted one or more times, for example once, twice or three times, by identical or different radicals. This applies likewise to heteroaryl radicals such as, for example, in the radical heteroarylalkyl. Examples of heteroaryl are furanyl, thienyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, indazolyl, quinolyl, isoquinolyl, phthalazinyl, quinoxalinyl, quinazolinyl and cinnolinyl.

Heteroaryl radicals include, in particular, 2- or 3-thienyl, 2- or 3-furyl, 1-, 2- or 3-pyrrolyl, 1-, 2-, 4- or 5-imidazolyl, 1-, 3-, 4- or 5-pyrazolyl, 1, 2, 3-triazol-1-,-4- or -5-yl, 1,2,4-triazol-1-, -3- or -5-yl, 1- or 5-tetrazolyl, 2-, 4- or 5-oxazolyl, 3-, 4- or 5-isoxazolyl, 1,2,3-oxadiazol-4- or -5-yl, 1,2,4-oxadiazol-3- or -5-yl, 1,3,4-oxadiazol-2-yl or -5-yl, 2-, 4- or 5-thiazolyl, 3-, 4- or 5-isothiazolyl, 1,3,4-thiadiazol-2- or -5-yl, 1,2,4-thiadiazol-3or -5-yl, 1,2,3-thiadiazol-4- or -5-yl, 2-, 3- or 4-pyridyl, 2-, 4-, 5- or 6-pyrimidinyl, 3- or 4-pyridazinyl, pyrazinyl, 1-, 2-, 3-, 4-, 5-, 6- or 7-indolyl, 1-, 2-, 4- or 5-benzimidazolyl, 1-, 3-, 4-, 5-, 6- or 7-indazolyl, 2-, 3-, 4-, 5-, 6-, 7- or 8-quinolyl, 1-, 3-, 4-, 5-, 6-, 7- or 8-isoquinolyl, 2-, 4-, 5-, 6-, 7- or 8-quinazolinyl, 3-, 4-, 5-, 6-, 7- or 8-cinnolinyl, 2-, 3-, 5-, 6-, 7- or 8-quinoxalinyl, 1-, 4-, 5-, 6-, 7- or 8-phthalazinyl. Also encompassed are the corresponding N-oxides of these compounds, i.e. for example 1-oxy-2-, 3- or 4-pyridyl.

Particularly preferred heteroaromatic radicals include 2- or 3-thienyl, 2- or 3-furyl, 1-, 2- or 3-pyrrolyl, 1-, 2-, 4- or 5-imidazolyl, 2-, 3-, 4-, 5-, 6-, 7- or 8-quinolyl, 1-, 3-, 4-, or 5-pyrazolyl, 2-, 3- or 4-pyridyl, 2- or 3-pyrazinyl 2-, 4-, 5- or 6-pyrimidinyl and 3- or 4-pyridazinyl.

The compounds of formula I may be isolated in the form of their salts. These are obtained by conventional methods by reaction with acids or bases. Examples of suitable acid addition salts in this connection include halides, especially hydrochlorides, hydrobromides, lactates, sulfates, citrates, tartrates, acetates, phosphates, methylsulfonates, benzenesulfonates, p-toluenesulfonates, adipates, fumarates, gluconates, glutamates, glycerolphosphates, maleates, benzoates, oxalates and pamoates and trifluoroacetates, in the case of the preparation of active ingredients preferably pharmaceutically suitable salts. If the compounds contain an acidic group, they can form salts with bases, for example alkali metal salts, preferably sodium or potassium salts, or ammonium salts, for example of salts with ammonia or organic amines or amino acids. They may also be in the form of a zwitterion.

List of Abbreviations:

| DMF | N,N-Dimethylformamide |
| DMSO | Dimethyl sulfoxide |
| dba | Dibenzylideneacetone |
| OAc | Acetate |
| M.p. | Melting point |
| MTB | tert-Butyl methyl ether |
| NMP | N-Methyl-2-pyrrolidone |
| dppf | 1,1'-Bis-(diphenylphosphino)-ferrocene |
| THF | Tetrahydrofuran |

EXAMPLES

Example 1 a) 4-Aminophenylsulfur pentafluoride

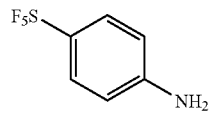

A solution of tin(II) chloride (1465 g., 7.73 mol) in concentrated (32 percent) aqueous HCl solution was heated with stirring to 80° C. and then, with ice cooling, 4-nitrophenylsulfur pentafluoride (584 g., 2.344 mol) was introduced in 8 portions over the course of 1 h. The internal temperature was kept below 100° C. during this. Subsequently, the mixture was stirred at an internal temperature of 85° C. for 1.5 h and then cooled to 45° C. over the course of a further hour. A mixture of ice (12 kg), NaOH (2 kg) and dichloromethane (1.5 l) was prepared and added to the reaction mixture with vigorous stirring. The phases were separated, the aqueous phase was extracted 3 times with 1 l of dichloromethane each time, and the combined organic phases were dried over $Na_2SO_4$ and evaporated in vacuo. 510 g (99%) of 4-aminophenylsulfur pentafluoride were obtained as a pale yellow crystalline powder, m.p. 63-65° C. (Bowden, R. D., Comina, P. J., Greenhall, M. P., Kariuki, B. M., Loveday, A., Philip, D. Tetrahedron 2000, 56, 3399: 56-59° C.).

$^1$H-NMR 400 MHz, CDCl$_3$; δ=3.99 (bs, 2H), 6.61 (d, J=9 Hz, 2H), 7.52 (d, J=9 Hz, 2H)ppm.

b) 4-Amino-3-bromophenylsulfur pentafluoride

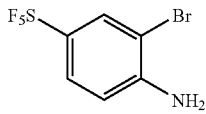

4-Aminophenylsulfur pentafluoride (510 g. 2.327 mol) was dissolved in dichloromethane (7 l), the solution was cooled to 5° C. and, while stirring, 1,3-dibromo-5,5-dimethylimidazolidine-2,4-dione (326 g. 1.14 mol) was introduced in several portions with ice cooling so that the internal temperature was kept at 3-8° C. (approx. 1 h). The mixture was then left to stir and warm to room temperature without external cooling for 1 h. The mixture was filtered through a bed of silica gel (volume about 1 l) and washed with dichloromethane (5.5 l), and the filtrate was evaporated in vacuo. About 700 g of a red-brown crystalline mass was obtained and was dissolved in n-heptane (600 ml) at 60° C. and then crystallized in a refrigerator at 4° C. Filtration with suction resulted in 590 g (85%) of 4-amino-3-bromphenylsulfur pentafluoride as brownish crystals, m.p. 59-59.5° C.

$^1$H-NMR 400 MHz, CDCl$_3$; δ=4.45 (bs, 2H), 6.72 (d, J=9 Hz, 1H), 7.49 (dd, J$_1$=9 HZ, J$_2$=2.5 Hz, 1H), 7.81 (d, J=2.5 Hz, 1H) ppm. C$_6$H$_5$BrF$_5$NS (298.07): calc. C 24.18, H 1.69, N 4.70; found C 24.39, H 1.45, N 4.77.

c) 4-Amino-3-methylphenylsulfur pentafluoride

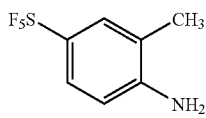

A mixture of Cs$_2$CO$_3$ (794 g, 2.7 mol), dimethoxyethane (2 l), water (300 ml) and trimethylboroxine (50 percent solution in THF, 225 g. 0.9 mol) was heated to 70° C., PdCl$_2$ (dppf)×CH$_2$Cl$_2$ (37 g. 45 mmol) was added, and a solution of 4-amino-3-bromophenylsulfur pentafluoride (270 g., 0.9 mol) in dimethoxyethane (400 ml) was added dropwise over the course of 2 h while the reaction mixture was heated to reflux. It was subsequently heated under reflux for a further 3 h and then cooled to room temperature, diluted with MTB ether (500 ml), filtered through a silica gel column (14×7 cm, 70-200 μm) and washed with MTB ether (2500 ml). The filtrate was evaporated in vacuo 490 g of a black, semicrystalline mass was obtained and was subjected to a steam distillation. A total of 5.5 l of condensate was collected, from which the crystals of the product separated out. The condensate was extracted 3× with MTB ether, and the combined organic phases were dried over Na$_2$SO$_4$ and evaporated in vacuo. 4-Amino-3-methylphenylsulfur pentafluoride (181 g. 76%) was obtained as colorless crystals, m.p. 65-66° C.

$^1$H-NMR 400 MHz, CDCl$_3$: δ=2.18 (s, 3 H), 3.92 (bs, 2 H), 6.60 (d, J=8.5 Hz, 1 H), 7.40 (dd, J$_1$=8.5 Hz, J$_2$=2.5 Hz, 1 H), 7.43 (d, J=2.5 Hz, 1 H) ppm C$_7$H$_8$F$_5$NS (233.20): calc. C 36.05, H 3.46, N 6.01; found C 36.43 H 3.30 N 6.09.

d) 4-Bromo-3-methylphenylsulfur pentafluoride

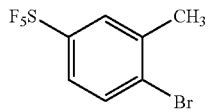

A mixture of tert-butyl nitrite (90 percent pure, 37 ml, 280 mmol) and CuBr$_2$ (35.8 g. 160 mmol) in acetonitrile (260 ml) was cooled to 5° C. and, while stirring and cooling with ice, a solution of 4-amino-3-methylphenylsulfur pentafluoride (30.9 g, 132.5 mmol) in MTB ether (140 ml) was added dropwise at 5-8° C. over the course of 1 h. Evolution of nitrogen started after about 2 min. The mixture was then allowed to warm with stirring to room temperature over the course of 1 h, a mixture of ice (250 g), 26 percent aqueous NH$_3$ solution (50 ml) and MTB ether (250 ml) was added, and the mixture was stirred for 10 min. The phases were separated, the aqueous was extracted 3× with MTB ether (150 ml each time), and the combined organic phases were shaken once with 400 ml of water. Drying with Na$_2$SO$_4$ and evaporation of the organic phase resulted in 39 g of 4-bromo-3-methylphenylsulfur pentafluoride as a red-brown oil which, according to 1H-NMR, was contaminated with 8 mol % of 4,5-dibromo-3-methylphenylsulfur pentafluoride, but was used further without further purification. Yield 89% based on a purity of 90%. For combustion analysis, a sample was purified by chromatography on silica gel (35-70 μm, heptane).

$^1$H-NMR 400 MHz, CDCl$_3$: δ=2.47 (s, 3 H), 7.43 (dd, J$_1$=9 Hz, J$_2$=3 Hz, 1 H), 7.62(m,2 H) ppm. Signals of 4,5-dibromo-3-methylphenylsulfur pentafluoride (contaminant): 2.56 (s, 3 H), 7.56 (d, J=2.5 Hz, 1 H), 7.85 (d, J=2.5 Hz, 1 H). C$_7$H$_6$BrF$_5$S (297.09): calc. C 28.30, H 2.04; found C 28.42, H 1.78.

e) 4-Cyano-3-methylphenylsulfur pentafluoride

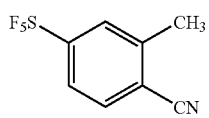

A mixture of 4-bromo-3-methylphenylsulfur pentafluoride (136.4 g, purity 80%, 0.367 mol), Zn(CN)$_2$ (72.8 g, 0.62 mol) and Zn dust (7.2 g, 0.11 mol) in dimethylacetamide (900 ml) and water (40 ml) was heated with stirring and nitrogen blanketing to 125° C., and PdCl$_2$(dppf)×CH$_2$Cl$_2$ (32.7 g, 40 mmol) was added. After stirring at 125° C. for one hour, PdCl$_2$(dppf)×CH$_2$Cl$_2$ (16.3 g, 20 mmol) and Zn dust (3.6 g, 55 mmol) were again added, and stirring was continued at 125° C. for 2 h. The mixture was then cooled to room temperature, diluted with n-heptane (400 ml) and stirred vigorously with addition of 5 N aqueous NH$_4$Cl solution (250 ml) and water (450 ml) for 15 min. The mixture was filtered with suction through a layer of kieselguhr, the phases were separated, and the aqueous was extracted 2× with n-heptane (200 ml). The combined organic phases were shaken with water (450 ml), dried over MgSO$_4$ and evaporated in vacuo. The resulting black residue was dissolved in 200 ml of n-heptane, filtered and again evaporated in vacuo. 78 g of a dark brown liquid were obtained and were purified by chromatography on a silica gel column (7×55 cm, 60-200 μm, n-heptane/dichloromethane 4:1 to 3:2). The first fraction obtained was 6.5 g of 4-bromo-3-methylphenylsulfur pentafluoride (precursor) as yellowish liquid, and then 71.1 g (80%) of 4-cyano-3-methylphenylsulfur pentafluoride as pale yellow oil.

$^1$H-NMR 400 MHz, CDCl$_3$: δ=2.65 (s, 3 H), 7.71 (m, 3H) ppm.

f) 2-Methyl-4-pentafluorosulfanylbenzoic acid

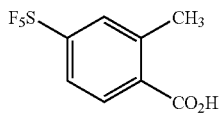

A mixture of 4-cyano-3-methylphenylsulfur pentafluoride (41.2 g, 169.4 g), NaOH (20.4 g, 510 mmol) and water (60 ml) in ethylene glycol (160 ml) was heated to 130° C. and stirred at this temperature for 4 h. It was then cooled to room temperature and diluted with MTB ether (150 ml) and water (250 ml), and the mixture was filtered with suction. The phases of the filtrate were separated, and the aqueous was acidified with concentrated aqueous HCl solution, and the precipitated solid was filtered off with suction. 41.1 g (93%) of 2-methyl-4-pentafluorosulfanylbenzoic acid were obtained as colorless crystals, m.p. 138-139° C.

$^1$H-NMR 400 MHz, DMSO-d$_6$: δ=2.60 (s, 3 H), 7.81 (dd, J$_1$=8.5 Hz, J$_2$=2 Hz, 1 H), 7.89 (d, J=2 Hz, 1 H), 7.97 (d, J=8.5 Hz, 1 H), 13.43 (bs, 1 H) ppm. C$_8$H$_7$F$_5$O$_2$S (262.20): calc. C 36.65, H 2.69; found C 36.85, H 2.59.

g) 2-Methyl-4-pentafluorosulfanylbenzoylguanidine

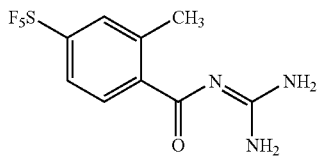

2-Methyl-4-pentafluorosulfanylbenzoic acid (77.5 g, 295 mmol) was suspended in toluene (300 ml), thionyl chloride (36 ml, 0.5 mol) and 5 drops DMF were added, and the mixture was heated under reflux with stirring for 2 h. It was then filtered with suction, the filtrate was evaporated in vacuo, the residue was taken up 2× in toluene (100 ml each time) and evaporated in vacuo each time. 78.8 g of the acid chloride were obtained as a pale brown liquid, which was used further without purification. Guanidine hydrochloride (172 g, 1.8 mol) was added to a solution of NaOH (84 g, 2.1 mol) in water (600 ml), and the mixture was cooled to −3° C. Then, while stirring and ice cooling, the solution of the crude acid chloride in dichloromethane (600 ml) was added dropwise over the course of 1 h. The mixture was left to stir at room temperature for a further 30 min, and then the precipitated solid was filtered off with suction, washed with dichloromethane and dried at room temperature in vacuo. 74.3 g (87%) of 2-methyl-4-pentafluorosulfanylbenzoylguanidine were obtained as beige crystal, m.p. 183-183.5° C.

$^1$H-NMR 400 MHz, CD$_3$OD: δ=2.51 (s, 3 H), 4.84 (bs, 5 H), 7.62 (m, 2 H), 7.65 (s, 1 H) ppm. C$_9$H$_{10}$F$_5$N$_3$OS (303.26): calc. C 35.65, H 3.32, N 13.86; found C 35.69, H 3.18, N 14.04.

What is claimed is:

1. A compound of the formula XI

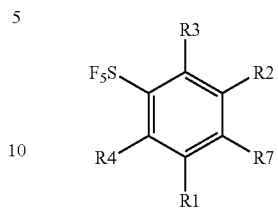

wherein:
R1 is hydrogen, alkyl having 1, 2, 3 or 4 carbon atoms, alkoxy having 1, 2, 3 or 4 carbon atoms, NR10R11, —O—(CH$_2$)$_n$—(CF$_2$)$_o$—CF$_3$ or —(SO$_m$)$_q$—(CH$_2$)$_r$—(CF$_2$)$_s$—CF$_3$;
R10 and R11 are, independently of one another, hydrogen, alkyl having 1, 2, 3 or 4 carbon atoms or —CH$_2$—CF$_3$;
m is zero, 1 or 2;
n, o, p, q, r and s are, independently of one another, zero or 1;
R2 is hydrogen, F, Cl, Br, I, —(SO$_h$)$_z$—(CH$_2$)$_k$—(CF$_2$)$_l$—CF$_3$ or alkyl having 1, 2, 3, 4, 5 or 6 carbon atoms;
h is zero, 1 or 2;
z is zero or 1;
k is zero, 1, 2, 3 or 4;
l is zero or 1;
R3 and R4 are, independently of one another hydrogen or F;
R7 is CN,
and the salts thereof.

2. The compound of claim 1 wherein R1 is hydrogen, alkyl having 1, 2, 3 or 4 carbon atoms, methoxy, ethoxy, NR10R11, —O—CH$_2$—CF$_3$ or —SO$_m$—(CH$_2$)$_r$—CF$_3$, wherein R10 and R11 are independently of one another hydrogen, alkyl having 1, 2, 3or 4 carbon atoms or —CH$_2$—CF$_3$; and where m is zero, 1 or 2 and r is zero or 1.

3. The compound of claim 2 wherein R1 is hydrogen or methyl.

4. The compound of claim 2 wherein R2 is hydrogen, F, Cl, Br, I, alkyl having 1, 2, 3 or 4 carbon atoms or —SO$_h$—(CH$_2$)$_k$—CF$_3$, wherein h is zero, 1 or 2 and k is zero or 1.

5. The compound of claim 4 wherein R2 is hydrogen.

6. The compound of claim 4 wherein R2 is selected from the group consisting of F, Cl, Br, and I.

7. The compound of claim 6 wherein R2 is Br.

8. A process for preparing a 4-acylguanidinophenyl-pentafluorosulfane comprising the steps of:
a) reacting a 4-aminophenyl-pentafluorosulfane with a halogenating agent under conditions effective to provide a 4-halophenyl-pentafluorosulfane;
b) reacting said 4-halophenyl-pentafluorosulfane with hydrogen cyanide or a salt thereof to provide a 4-nitrilephenyl-pentafluorosulfane;
c) hydrolyzing said 4-nitrilephenyl-pentafluorosulfane to provide a 4-carboxyphenyl-pentafluorosulfane; and
d) reacting said 4-carboxyphenyl-pentafluorosulfane with guanidine to provide said 4-acylguanidinophenyl-pentafluorosulfane.

9. A process according to claim 8, wherein before step a), said method comprises the steps of:
reacting said 4-aminophenyl-pentafluorosulfane with a halogenating agent under conditions effective to prove a 2-halo-4-aminophenyl-pentafluorosulfane; and reacting said 2-halo-4-aminophenyl-pentafluorosulfane with a nucleophile or organometallic compound effective to replace said 2-halo substituent with an R2 group, wherein:

R2 is —$(SO_h)_z$—$(CH_2)_k$—$(CF_2)_l$—$CF_3$, alkyl having 1, 2, 3, 4, 5 or 6 carbon atoms, cycloalkyl having 3, 4, 5, 6, 7 or 8 carbon atoms, in which 1, 2, 3 or 4 hydrogen atoms may be replaced by fluorine atoms;

h is zero, 1 or 2;
z is zero or 1;
k is zero, 1, 2, 3 or 4;
l is zero or 1;

or R2 is —$(CH_2)_t$-phenyl or —O-phenyl, which are unsubstituted or substituted by 1, 2 or 3 radicals selected from the group consisting of —$O_u$—$(CH_2)_v$—$CF_3$, alkoxy having 1, 2, 3 or 4 carbon atoms, alkyl having 1, 2, 3 or 4 carbon atoms and —$SO_2CH_3$;

t is zero, 1, 2, 3 or 4;
u is zero or 1;
v is zero, 1, 2 or 3;

or R2 is —$(CH_2)_w$-heteroaryl which is unsubstituted or substituted by 1, 2 or 3 radicals selected from the group consisting of —$O_x$—$(CH_2)_y$—$CF_3$, alkoxy having 1, 2, 3 or 4 carbon atoms and alkyl having 1, 2, 3 or 4 carbon atoms, —$SO_2CH_3$;

w is zero, 1, 2, 3 or 4;
x is zero or 1; and
y is zero, 1, 2 or 3.

10. The process of claim 8 wherein said 4-aminophenyl-pentafluorosulfane is formed by reacting a 4-nitrophenyl-sulfurpentafluoride with tin(II) chloride in a concentrated HCl solution.

* * * * *